United States Patent [19]
Lee et al.

[11] Patent Number: 6,017,702
[45] Date of Patent: Jan. 25, 2000

[54] CHAIN-TERMINATION TYPE NUCLEIC ACID SEQUENCING METHOD INCLUDING 2'-DEOXYURIDINE-5'-TRIPHOSPHATE

[75] Inventors: Linda G. Lee, Palo Alto; Barnett B. Rosenblum, San Jose, both of Calif.

[73] Assignee: The Perkin-Elmer Corporation, Foster City, Calif.

[21] Appl. No.: 08/785,581

[22] Filed: Jan. 21, 1997

Related U.S. Application Data

[60] Provisional application No. 60/032,608, Dec. 5, 1996, abandoned.

[51] Int. Cl.$^7$ .............................. C12Q 1/68; C07H 21/04
[52] U.S. Cl. .......................... 435/6; 435/810; 536/24.33; 935/8; 935/78
[58] Field of Search .............................. 435/6, 91.2, 91.5, 435/91, 810; 536/24.33; 935/8, 78; 436/800

[56] References Cited

U.S. PATENT DOCUMENTS

| | | | |
|---|---|---|---|
| 5,035,996 | 7/1991 | Hartley | 435/6 |
| 5,187,085 | 2/1993 | Lee | 435/91 |
| 5,405,747 | 4/1995 | Jett et al. | 435/6 |
| 5,418,149 | 5/1995 | Gelfand et al. | 435/91.2 |
| 5,538,848 | 7/1996 | Livak et al. | 435/5 |
| 5,659,025 | 8/1997 | Engels et al. | 536/23.1 |
| 5,691,146 | 11/1997 | Mayrand | 435/6 |

OTHER PUBLICATIONS

Voss et al. Meth. Mol. Cell. Biol. 3:30–34, 1992.

Amersham Catalog 1994 pp. 74–83, 1994.

Pu et al., "Uracil interference, a rapid and general method for defining protein–DNA interactions involving the 5–methyl group of thymines: The GCN4–DNA complex," *Nucl. Acids Res.* 20(4):771–775 (1992).

Devchand et al., "Uracil–DNA glycosylase as a probe for protein–DNA interactions," *Nucl. Acids Res.* 21(15):3437–3443 (1993).

Slupphaug et al. Analytical Biochemistry, 211: 164–169 (1993) Low Incorporation of dUMP by Some Thermostable DNA Polymerases May Limit Their Use in PCR Amplifications.

Longo et al. Gene, 93: 125–128, (1990) Use of Uracil DNA Glycosylase to Control Carry–Over Contamination in Polymerase Chain Reactions.

Voss et al. Methods in Molecular and Cellular Biology, 3:153–155 (1992) Automated DNA Sequencing System Resolving 1,000 Bases with Fluorescein–15–*dATP as Internal Label.

*Primary Examiner*—W. Gary Jones
*Assistant Examiner*—Debra Shoemaker
*Attorney, Agent, or Firm*—Paul D. Grossman

[57] ABSTRACT

A chain-termination type DNA sequencing method is disclosed wherein deoxynucleotide 2'-deoxythymidine-5'-triphosphate is replaced by 2'-deoxyuridine-5'-triphosphate, or analogs thereof Kits for performing the method are also provided.

7 Claims, 5 Drawing Sheets

5-CFB-dTMR-2

5-CFB-dROX-2

6-CFB-dTMR-2

6-CFB-dROX-2

5-CFB-dR110-2

5-CFB-dR6G-2

6-CFB-dR110-2

6-CFB-dR6G-2 ddT-EO-5CFBdTMR2 ddT-EO-6CFBdTMR2 ddTTP-EO-6FAM-B-dTMR2

109  113    119 122   128 131    137      144 146  151 154
Base dTTP 109   113    119 122   128 131    137     144 146   151 154
Base dUTP ddTTP-EO-5FAM-B-dTMR2 dTTP dUTP

CHAIN-TERMINATION TYPE NUCLEIC ACID SEQUENCING METHOD INCLUDING 2'-DEOXYURIDINE-5'-TRIPHOSPHATE

This application claims priority to U.S. provisional patent application Ser. No. 60/032,608 filed Dec. 5, 1996.

FIELD OF THE INVENTION

This invention relates to methods and kits for nucleic acid sequencing. More specifically, this invention relates to methods and kits for chain-termination type DNA sequencing wherein a deoxynucleotide 2'-deoxythymidine-5'-triphosphate is replaced by a 2'-deoxyuridine-5'-triphosphate, or analogs thereof

REFERENCES

ABI PRISM™ 373DNA *Sequencing-System User's Manual*, p/n 903204 (June, 1994)

ABI PRISM™ *Dye Primer Cycle Sequencing Core Kit with AmpliTaq® DNA Polyrnerase, FS, Protocol*, Revision C, p/n 402114 (1996)

ABI PRISM™ *Dye Terminator Cycle Sequencing Core Kit Protocol*, PE Applied Biosystems, Revision A, p/n 402116 (1995)

Bergot, et al., U.S. Pat. No. 5,366,860 (1994)

Connell et al., *Biotechniques*, 5(4): 342–348 (1987)

Eckstein ed., *Oligonucleotides and Analogs*, Chapters 8 and 9, IRL Press (1991)

Hobbs, et al., U.S. Pat. No. 5,151,507 (1992)

Khan et al., U.S. patent application Ser No. 08/696,808 (1996)

Lee et al, *Nucleic Acids Research*, 20(10): 2471–2483 (1992)

Lee et al., U.S. patent application Ser. No. 08/726,462 (1996)

Murray, *Nucleic Acids Research*, 17(21): 8889 (1989)

Prober et al., *Science*, 238: 336–341 (1987)

Scheit, Nucleotide Analogs, John Wiley (1980)

Smith et al., U.S. Pat. No. 5,171,534 (1992)

Smith et al., U.S. Pat. No. 5,171,534 (1992)

Trainor, *Anal. Chem.*, 62: 418–426 (1990)

BACKGROUND

DNA sequencing has become a vitally important technique in modern biology and biotechnology, providing information relevant to fields ranging from basic biological research to drug discovery to clinical medicine. Because of the large volume of DNA sequence data to be collected, automated techniques have been developed to increase the throughput and decrease the cost of DNA sequencing methods (Smith; Connell; Trainor).

A preferred automated DNA sequencing method is based on the enzymatic replication with chain termination technique developed by Sanger (Sanger). In Sanger's chain-termination technique, the DNA sequence of a single-stranded template DNA is determined using a DNA polymerase to synthesize a set of polynucleotide fragments wherein the fragments (i) have a sequence complementary to the template sequence, (ii) vary in length by a single nucleotide, and (iii) have a 5'-end terminating in a known nucleotide, e.g., A, C, G, or T. In the method, an oligonucleotide primer is annealed to a 3'-end of a template DNA to be sequenced, a 3'-end of the primer serving as an initiation site for polymerase mediated polymerization of a complementary polynucleotide fragment. The enzymatic polymerization step is carried out by combining the template-primer hybrid with each of the four 2'-deoxynucleotide-5'-triphosphate nucleotides, A, G, C, and T ("dNTPs"), a DNA polymerase enzyme, and a 2',3'-dideoxynucleotide triphosphate ("ddNTP") terminator. The incorporation of the terminator forms a fragment which lacks a hydroxy group at the 3'-terminus and thus can not be further extended by the polymerase, i.e., the fragment is "terminated". The competition between the ddNTP and its corresponding dNTP for incorporation results in a distribution of different-sized fragments, each fragment terminating with the particular terminator used in the reaction. To determine the complete DNA sequence of the template, four parallel reactions are run, each reaction using a different ddNTP terminator. To determine the size distribution of the fragments, the fragments are separated by electrophoresis such that fragments differing in size by a single nucleotide are resolved.

In a modern variant of the classical Sanger chain-termination technique, the nucleotide terminators, or the oligonucleotide primers, are labeled with fluorescent dyes (Prober; Hobbs; Smith). Several advantages are realized by utilizing such dye-labeled terminators, in particular: (i) problems associated with the storage, use and disposal of radioactive isotopes are eliminated; (ii) the requirement to synthesize dye-labeled primers is eliminated; and, (iii) when using a different dye label for each A,G,C, or T nucleotide, all four reactions can be performed simultaneously in a single tube.

While the Sanger chain-termination sequencing method has proven very effective, several problems remain with respect to optimizing its performance. One such problem, particularly when using dye-labeled terminators, is the sequence-dependent variability of the incorporation of labeled terminator into the primer extension products, particularly in the case of T-terminated fragments. This variability of incorporation leads to variable peak heights in the resulting electropherogram. Such peak height variability may lead to several problems. First, such variability decreases the sensitivity of the method, which is limited by the ability to detect the weakest peaks. Second, such variability creates difficulties in determining whether a peak having a weak signal is a true signal due to the incorporation of a chain-terminating agent, or an artifact due to a pause site in the DNA where the polymerase has dissociated. Third, such variations decrease the accuracy in determining the identity of closely spaced bands since the strong signal of one band may mask the weak signal of its neighbor. Each of these problems become particularly acute when automated base calling algorithms are applied to the data.

SUMMARY

The present invention is directed towards our discovery of an improved Sanger chain-termination polynucleotide sequencing method wherein a deoxynucleotide 2'-deoxythymidine- 5'-triphosphate is replaced by a 2'-deoxyuridine-5'-triphosphate, or analogs thereof.

It is an object of the invention to provide a Sanger chain-termination polynucleotide sequencing method wherein the variability of peak heights in an electropherogram is substantially reduced.

In a first aspect, the foregoing and other objects of the invention are achieved by a chain-termination type nucleic acid sequencing method comprising the following steps: (i) providing a template nucleic acid; (ii) annealing an oligonucleotide primer to a portion of the template nucleic acid thereby forming a primer-template hybrid; (iii) adding a primer-extension reagent to the primer-template hybrid for extending the primer and forming a primer extension product, where the primer extension reagent includes a 2'-deoxyuridine-5'-triphosphate nucleotide; and (iv) adding a terminator to the primer-template hybrid for causing specific termination of the primer extension product. In a preferred embodiment of the method, the terminator has a label attached thereto, e.g., a fluorescent label.

In a second aspect, the invention includes a kit for performing the above-described chain-termination type nucleic acid sequencing method. The kit includes (i) an oligonucleotide primer; (ii) a primer-extension reagent for extending the primer and forming a primer extension product, the primer extension reagent including a 2'-deoxyuridine-5'-triphosphate nucleotide; and (iii) a terminator for causing specific termination of the primer extension product. In a preferred embodiment of the kit, the terminator has a label attached thereto, e.g., a fluorescent label.

These and other objects, features, and advantages of the present invention will become better understood with reference to the following description, drawings, and appended claims.

DETAILED DESCRIPTION OF THE PREFERRED EMBODIMENTS

Figures 1, 1A:
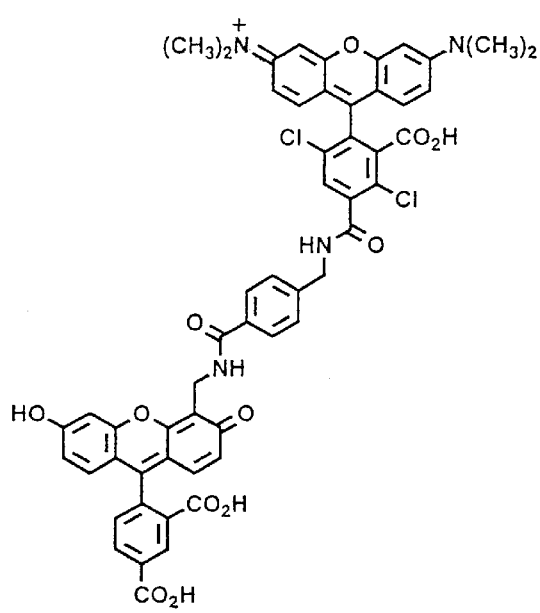
FIGS. 1A-1 through 1A-4 and show the structures of several exemplary energy transfer dyes.
Figures 1, 1A, 2:
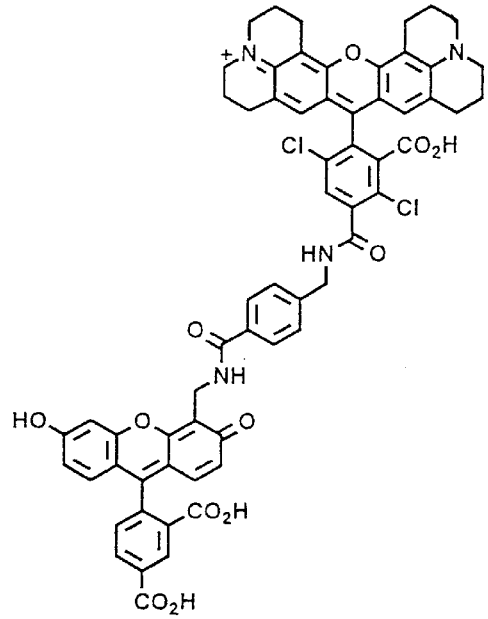
Figures 1, 1A, 2, 3:
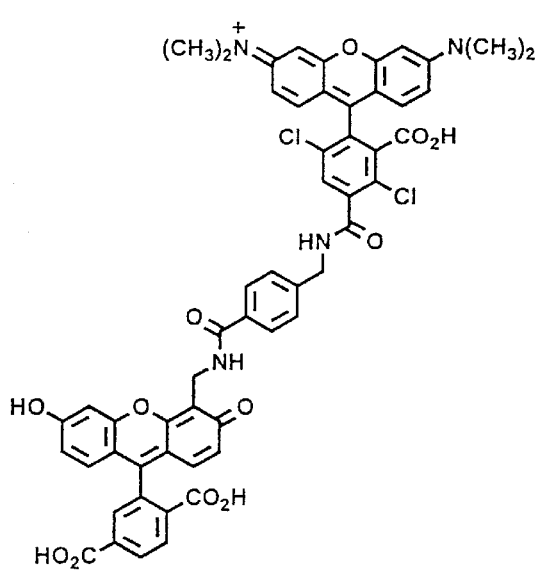
Figures 1, 1A, 2, 3, 4:
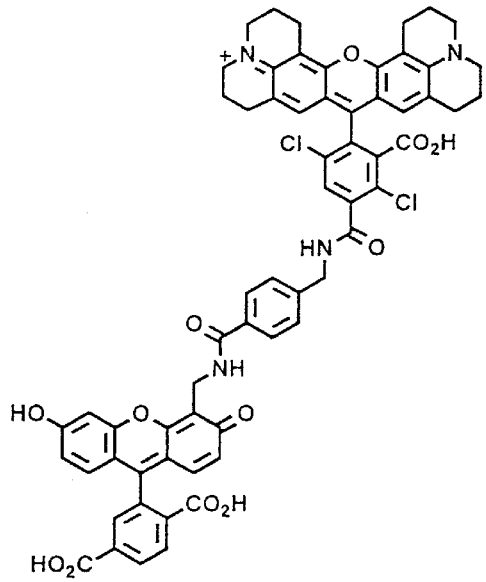
Figures 1, 1B:
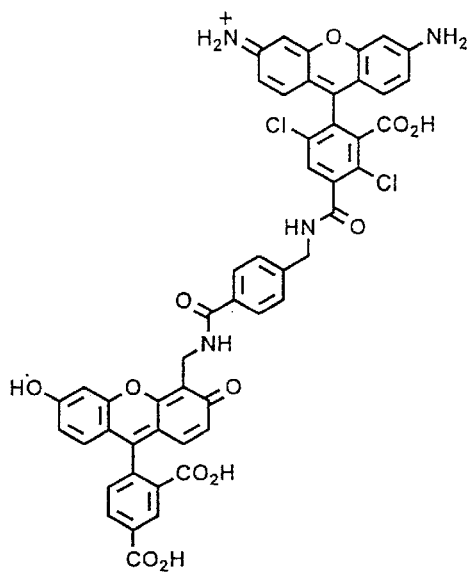
Figures 1, 1B, 2:
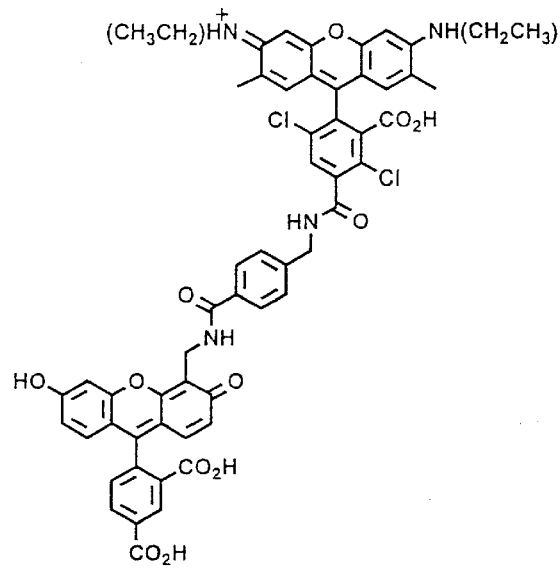
Figures 1, 1B, 2, 3:
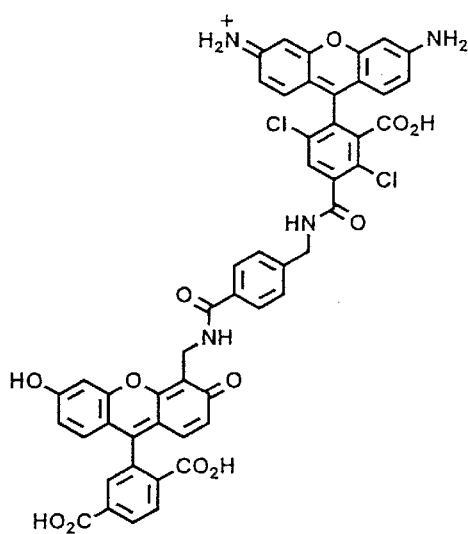
Figures 1, 1B, 2, 3, 4:
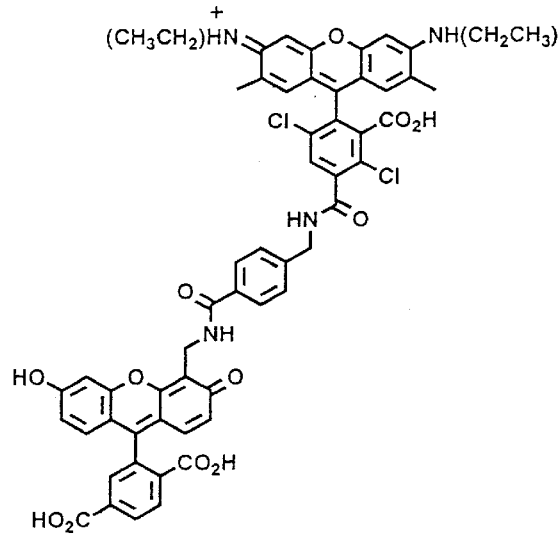

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises methods and kits for performing chain-termination type DNA sequencing wherein a 2'-deoxythymidine-5'-triphosphate nucleotide (dTTP) is replaced by a 2'-deoxyuridine-5'-triphosphate nucleotide (dUTP), or analogs thereof The method and kits find particular application in chain-termination type DNA sequencing reactions where a label is attached to a dideoxynucleotide terminator.

The invention is based in part on the discovery that by replacing a 2'-deoxythymidine-5'-triphosphate nucleotide with a 2'-deoxyuridine-5'-triphosphate nucleotide in a chain-termination type DNA sequencing reaction, when the reaction products are resolved by electrophoresis, there is significantly less variation in the amount of each reaction product produced, resulting in an electropherogram characterized by more even peak heights, thereby facilitating the application of automated base-calling algorithms.

I. Definitions

Unless stated otherwise, the following terms and phrases as used herein are intended to have the following meanings:

The term "label" refers to a moiety that, when attached to a nucleoside or polynucleotide of the invention, render such nucleoside or polynucleotide detectable using known detection means. Exemplary labels include fluorophores, chromophores, radioisotopes, spin-labels, enzyme labels, chemilumincecent labels, and the like, which allow direct detection of a labeled compound by a suitable detector, or, a ligand, such as an antigen, or biotin, which can bind specifically with high affinity to a detectable anti-ligand, such as a labeled antibody or avidin. Preferably the labels are fluorescent dyes such as fluorescein-type or rhodanine-type dyes (Lee; Menchen).

The term "nucleoside" refers to a compound of a purine, deazapurine or pyrimidine nudeoside base, e.&, adenine, guanine cytosine, uracil, deazaadenine , deazaguanosine and the like, linked to a pentose at the 1' position, including 2'-deoxy and 2'-hydroxyl forms (Stryer). The term "nucleotide" as used herein refers to a phosphate ester of a nuleoside, e.g., triphosphate esters, wherein the most common site of esterification is the hydroxyl group attached at the C-5 position of the pentose. Many times in the present disclosure the term nucleoside will be intended to include both nucleosides and nucleotide. "Analogs" in reference to nucleosides include synthetic analogs having modified base moieties, modified sugar moieties, and/or modified phosphates ester moieties, e.g., as described elsewhere (Scheit; Eckstein).

As used herein, the terms "polynucleotide" or "oligonucleotide" refer to linear polymers of natural nucleotide monomers or analogs thereof, including double and single stranded deoxyribonucleotides, ribonucleotides, $\alpha$-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., H, $NH_4$, Na, and the like if such counterions are present. Polynucleotides typically range in size from a few monomeric units, e.g. 8–40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" demotes thymidine, unless otherwise noted.

The term "oligonucleotide primer" refers to an oligonucleotide or polynucleotide which, when annealed to a template nucleic acid, is capable of being extended from a 3'-end in the presence of primer extension reagents. Typically, an oligonucleotide primer will include a hydroxyl group at the 3'-position of a 3'-terminal nucleotide.

The term "phosphate analog" refers to analogs of phosphate wherein the phosphorous atom is in the $^{+5}$ oxidation state and one or more of the oxygen atoms is with a non-oxygen moiety, exemplary analogs including phosphorothioate, phosphorodhioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present.

As used herein the term "primer-extension reagent" means a reagent including components necessary to effect the enzymatic template-mediated extension of an oligonucleotide primer. Preferably, primer extension reagents include: (i) a polymerase enzyme, e.g., a thermostable polymerase enzyme such as Taq polymerase; (ii) a buffer; and (iii) 2'-deoxynucleotide triphosphates, e.g., 2'-deoxyuridine-5'-triphosphate, 2'-deoxyguanosine-5'-triphosphate, 2'-deoxy-7-deazadeoxyguanosine-5'-triphosphate, 2'-deoxyadenosine-5'-triphosphate, 2'-deoxythymidine-5'-triphosphate, 2'-deoxycytidine-5'-triphosphate.

As used herein, the term "terminator" refers to a species that when incorporated into a primer extension product blocks further elongation of the product. Exemplary terminators include 2',3'-dideoxynucleotides, e.g., 2',3'-dideoxyguanosine-5'-triphosphate, 7-deaza-2',3'-dideoxyguanosine-5'-triphosphate, 2',3'-dideoxyadenosine-5'-triphosphate, 2',3'-dideoxythymidine-5'-triphosphate, and 2',3'-dideoxycytidine-5'-triphosphate.

As used herein, the term "template nucleic acid" refers to any nucleic acid which can be presented in a single stranded form and is capable of annealing with a primer oligonucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere (ABI PRISM™ Dye Primer Cycle Sequencing Core Kit Protocol).

The term "fluorescein-type dyes" refers to a class of xanthene dye molecules which include the following fused three-ring system:

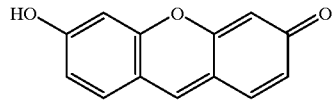

where a wide variety of substitutions are possible at each deoxy ring position. A particularly preferred subset of fluorescein-types dyes include the 4,7,-dichlorofluoresceins (Menchen). Examples of flourescein-type dyes used as fluorescent labels in DNA sequencing methods include 6-carboxyfluorescein (6-FAM), 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2',4',5',7'-tetrachlorofluorescein (ZOE). Many times the designation -1 or -2 is placed after an abbreviation of a particular dye, e.g., HEX-1. The "-1" and "-2" designations indicate the particular dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1 M triethylammonium acetate to 35% acetonitrile/65% 0.1 M triethylammonium acetate,.

The term "rhodamine-type dyes" refers to a class of xanthene dye molecules which include the following fused three-ring system:

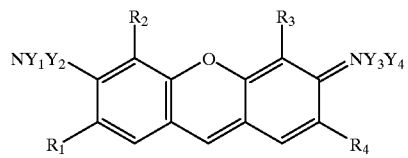

where preferably $Y_1$–$Y_4$ taken separately are hydrogen or lower alkyl, or, when taken together, $Y_1$ and $R_2$ is propano and $Y_2$ and $R_1$ is propano, or, when taken together, $Y_3$ and $R_3$ is propano and $Y_4$ and $R_4$ is propano. A wide variety of substitutions are possible at each deoxy ring position including the $R_1$–$R_4$ positions. Exemplary rhodamine type dyes useful as nucleoside labels include tetramethylrhodamine (TAMRA), 4,7-dichlorotetramethyl rhodamine (DTAMRA), rhodamine X (ROX), rhodamine 6G(R6G), rhodamine 110 (R110), and the like (Bergot; Lee 1992).

The term "energy transfer dye" refers to a class of fluorescent dyes comprising a donor dye which absorbs light at a first wavelength and emits excitation energy in response, an acceptor dye which is capable of absorbing the excitation energy emitted by the donor dye and fluorescing at a second wavelength in response, and a linker which connects the donor dye and the acceptor dye (Lee 1996). The structure of several energy transfer dyes are shown in FIGS. 1A-1 through 1A-4 and 1B-1 through 1B-4.

II. Sequencing Method

In a first aspect, the present invention comprises a Sanger chain-termination polynucleotide sequencing method using a modified primer extension reagent in which a 2'-deoxythymidine-5'-triphosphate nucleotide is replaced by a 2'-deoxyuridine-5'-triphosphate nucleotide, or analogs thereof.

The sequencing method of the invention is carried out using essentially the same procedures as are used in a typical sequencing reaction (ABI PRISM™ Dye Terminator Cycle Sequencing Core Kit). Generally, to perform a Sanger chain-termination reaction according to the invention, a template solution (e.g., a PCR reaction product) and a sequencing primer is mixed with primer-entension reagents comprising buffer, a deoxynucleotide/labeled dideoxynucleotide mixture including dUTP in place of dTTP, and 2 a polymerase enzyme. Optionally, the reaction is thermocycled in order to linearly amplify the amount of primer extension product produced. See Example 1 for a more detailed description of a preferred protocol.

It is preferred that no dTTP be present in the primer extension reagent. If both dTTP and dUTP are present, the primer extension products contain a distribution of both T and U nucleotides. Because T and U nucleotides contribute differently to the electrophoretic mobility of a primer extension product, such a mixture drastically complicates the electrophoretic analysis of the fragments by causing there to be multiple peaks for each fragment of a given size. For example, a 500-nucleotide fragment containing 100 Ts could possibly generate up to 100 different electrophoretic peaks rather then a single peak!

Exemplary DNA polymerases which may be used in the present method include Taq DNA polymerases including mutants thereof, T4 DNA polymerase, Klenow Fragment of DNA Polymerase I, Pfu DNA polymerase, and the like. Preferably, the polymerase is AmpliTaq FS DNA polymerase.

Preferably the labels used to label the primer extension products are fluorescent molecules. More preferably, the labels are fluorescein-type or rhodamine-type fluorescent molecules. Most preferably, the labels are energy transfer dyes. In a preferred embodiment of the invention, a label is attached to a didexoynucleotide terminator.

Preferably, the reaction products are separated by electrophoresis and detected by laser excited fluorescence using an automated DNA sequencing apparatus according to published protocols, e.g., using an ABI PRISM Model 373 DNA Sequencer (ABI PRISM™ 373 DNA Sequencing System).

III. Kits

In a second aspect, the present invention includes kits for conveniently carrying out the method of the invention. The kits include a primer extension reagent wherein dTTP has been removed and dUTP has been added. Optionally, the kits may include an oligonucleotide primer as well. In a preferred embodiment, the kits further include a standard template nucleic acid useful for determining the activity of the primer extension reagent.

IV. Examples

The invention will be further clarified by a consideration of the following examples, which are intended to be purely exemplary of the invention and not to in any way limit its scope.

EXAMPLE 1

Comparison of Peak Height Uniformity Between Reactions Using dTTP and dUTP Nucleotides To test the effect of replacing dTTP with dUTP on the results of a primer extension reaction, dye-labeled terminator reactions with T-termination were performed using a primer extension reagent including either dTTP or dUTP, and the uniformity of peak heights in an electropherogram of the resulting reaction products was compared.

Dye-terminator primer extension reactions were performed using AmpliTaq DNA Polymerase, FS following protocols provided in the ABI PRISM™ Dye Terminator Cycle Sequencing Core Kit Manual (PE Applied Biosystems p/n 402116). (The FS enzyme is a recombinant Thermus aquaticus DNA polymerase having two point mutations—G46D and F667Y). All primers and primer extension reagents (including buffer and AmpliTaq DNA Polymerase, FS enzyme), except the modified dNTP mix and dye-labeled terminators, were from an ABI PRISM-™ Dye Terminator Core Kit (PE Applied Biosystems p/n 402117). The dye-labeled T-terminators comprised an energy transfer dye linked to a dideoxy T-terminator through a propargylethoxyamino linker (Lee, 1996; Khan). A premix of reaction components was prepared as shown in the following table wherein all quantities are given on a per reaction basis:

| | |
|---|---|
| 5X Buffer[a] | 4.0 μL |
| dNTP mix[b] | 1.0 μL |
| pGEM ® -3Zf(+)template, 0.2 μg/μL | 5.0 μL |
| -21 M13 (forward) primer, 0.8 pmol/μL | 4.0 μL |
| AmpliTaq DNA Polymerase, FS[c] | 0.5 μL |
| H$_2$O | 0.5 μL |

[a]400 mM TRIS-HCl, pH 9; 10 mM MgCl$_2$.
[b]The standard dNTP mix consisted of 2 mM each of dATP, dCTP, and dTTP and 10 mM dITP. The modified dNTP mix was the same as the standard mix except that 2 mM dUTP was substituted for the 2 mM dTTP.
[c]8 Units/μl.

Reactions were assembled in 0.5 ml tubes adapted for the Perkin-Elmer 480 DNA Thermal Cycler (PE Applied Biosystems p/n N801–100). Reaction volumes were 20 μL, including 15 μL of the above-described reaction premix, from 1 to 1000 pmol of a dye-labeled terminator, and a sufficient volume of water to bring the total reaction volume up to 20 μl. The exact amount of dye-labeled terminator added to each reaction depended upon the particular dye-terminator used. 30 μL of mineral oil was added to the top of each reaction to prevent evaporation. Reactions were thermocycled as follows: 96° C. for 30 sec, 50° C. for 15 sec, and 60° C. for 4 min, for 25 cycles; followed by a 4° C. hold cycle.

All reactions were purified by spin-column purification on Centri-Sep spin columns according to manufacturer's instructions (Princeton Separations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300×g for 2 minutes, removed from the wash tube, and inserted into a sample collection tube. The reaction mixture was carefully removed from under the oil and is loaded onto the gel material. Columns were centrifuged in a variable speed microcentrifuge at 1300×g for 2 minutes. Eluted samples were then dried in a vacuum centrifuge.

Prior to loading onto a sequencing gel, the dried samples were resuspended in 25 μL of Template Suppression Reagent (PE Applied Biosystems p/n 401674), vortexed, heated to 95° C. for 2 minutes, cooled on ice, vortexed again, and centrifuged (13,000×g). 10 μL of the resuspended sample was aliquoted into sample vials (PE Applied Biosystems p/n 401957) adapted for the PE ABI PRISM™ 310 Genetic Analyzer (PE Applied Biosystems p/n 310-00-100/120). Electrophoresis on the 310 Genetic Analyzer was performed with sieving polymers and caries specially adapted for DNA sequencing analysis (PE Applied Biosystems p/n 402837 (polymer) and p/n 402840 (capillary)). In each case, the sieving polymer included nucleic acid denaturants. Samples were electrokinetically injected onto the capillary for 30 sec at 2.5 kV, and run for 2 hr at 12.2 kV with the outside wall of the capillary maintained at 50° C.

Figure 2A:
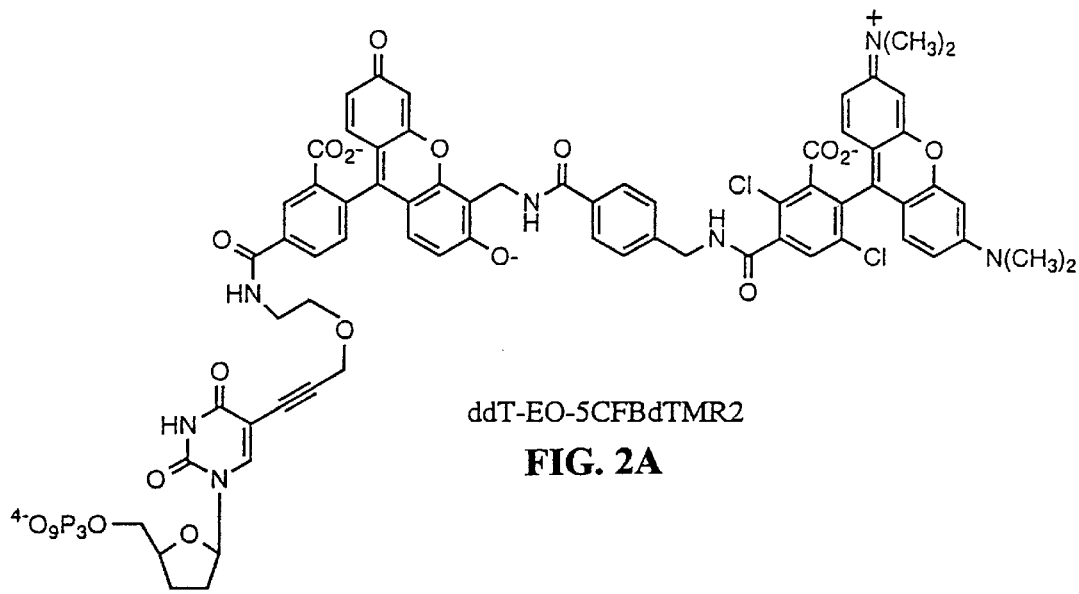
FIGS. 2A and 2B shows the structure of the dye-labeled terminators ddTTP-EO-6FAM-B-dTMR2 and ddTTP-EO-5FAM-B-dTMR2.
Figure 2B:
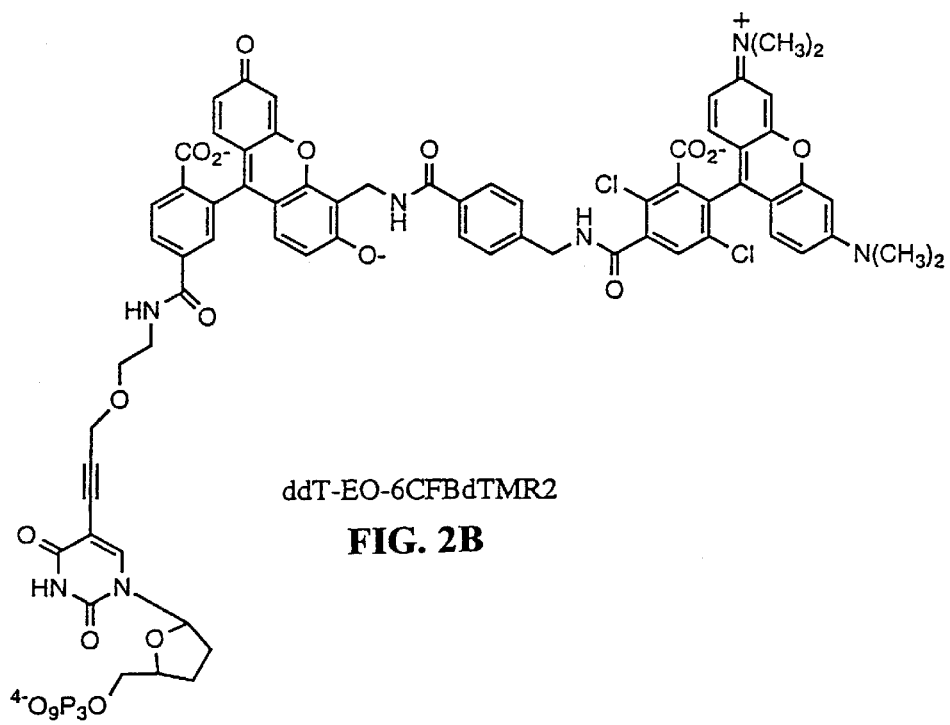

The dye-terminator primer extension reactions using dTTP or dUTP in the dNTP mix were compared using two different dye-labeled dideoxy T-terminators: ddTTP-EO-6FAM-B-dTMR2 and ddTTP-EO-5FAM-B-dTMR2, the structures of which are shown in FIG. 2A and 2B. (Note that the only difference between the two terminators is the FAM isomer used, i.e., 5-FAM or 6-FAM). The first 214 nucleotides were examined in each case. The parameters compared were mean peak height, standard deviation in peak height, relative error in peak height, where relative error is defined as the standard deviation divided by the mean peak height, and the percentage of "noisy" peaks, where noisy peaks are defined as peaks having a peak height of between 3 and 6 times the magnitude of the baseline noise.

Figure 3A:
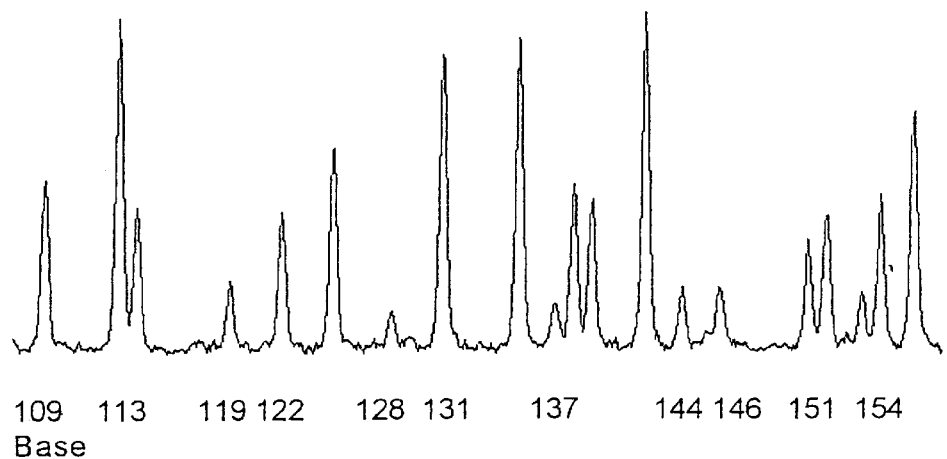
FIGS. 3A and 3B and FIGS. 4A and 4B show electropherograms comparing peak height variability in sequencing reactions containing dTTP (FIGS. 3A and 4B) or dUTP (FIGS. 3B and 4B) using two different dye-labeled dideoxynucleotide terminators.
Figure 3B:
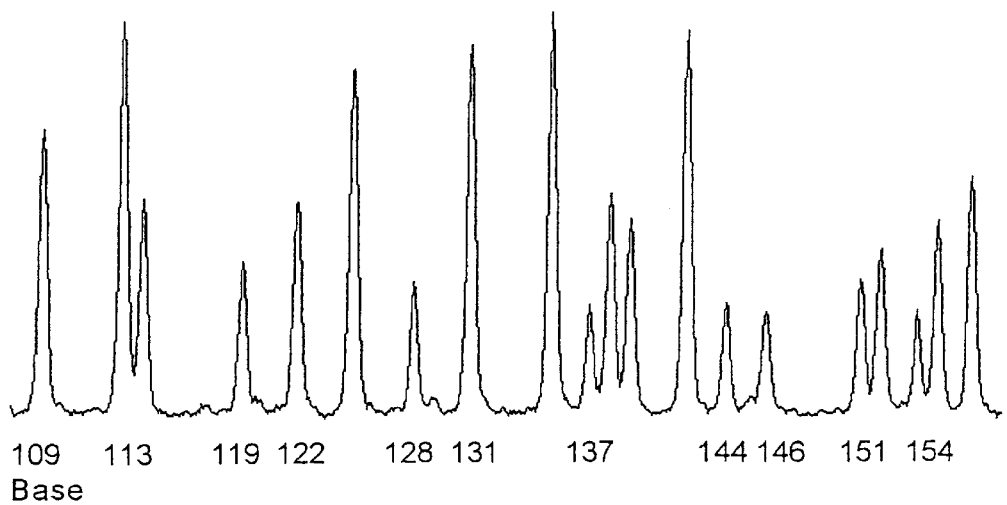

For the ddTTP-EO-6FAM-B-dTMR2 terminator in the presence of dTTP, the mean peak height was 631, the standard deviation was 355, the relative error was 0.563, and the percentage of noisy peaks was 32.7% of the total detected peaks. In the presence of dUTP, the mean peak height was 1791, the standard deviation was 841, the relative error was 0.47, and the percentage of noisy peaks was 21.8% of the total detected peaks. A portion of an electropherogram of the products of the dTTP reaction (top) and the dUTP reaction (bottom) using the ddTTP-EO-6FAM-B-dTMR2 terminator is shown in FIG. 3A and 3B. In these figures, bases 109, 119, and 128 show increased peak height relative to adjacent peaks when using dUTP such that these peaks are now no less than a third the height of the tallest peak where in the presence of dTTP they were less than 25% the height of the tallest peak. Peaks at bases 137, 144, 146, and 154 also show increased relative peak height in the presence of dUTP as compared to dTTP, however the increase was not as great as for the other peaks.

Figure 4A:
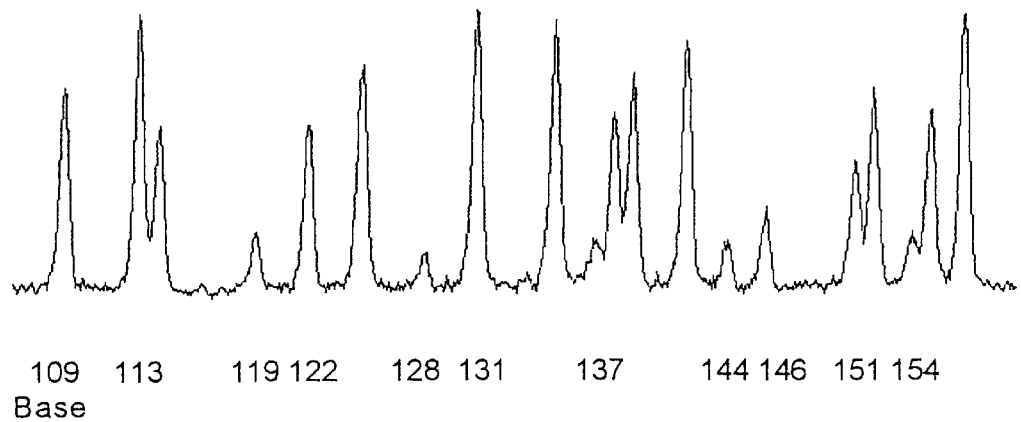
Figure 4B:
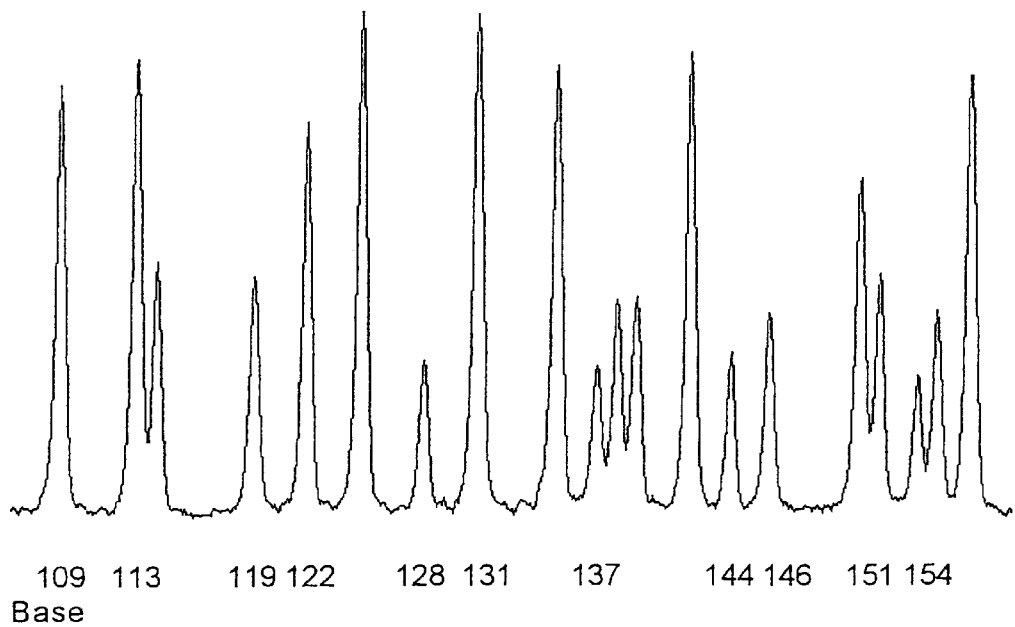

For the ddTTP-EO-5FAM-B-dTMR2 terminator in the presence of dTTP, the mean peak height was 635, the standard deviation was 319, the relative error was 0.5, and the percentage of noisy peaks was 17.6% of the total detected peaks. In the presence of dUTP, the mean peak height was 1694, the standard deviation was 662, the relative error of 0.39, and remarkably, no noisy peaks were detected. An electropherogram of the products of the dTTP reaction (top) and the dUTP reaction (bottom) using the ddTTP-EO-5FAM-B-dTMR2 terminator is shown in FIGS. 4A and 4B. In these figures, bases 109 and 119 show increased peak height relative to adjacent peaks when dUTP was used, such that these peaks are now no less than a third the height of the tallest peak, where in the presence of dTTP they were less than 25% the height of the tallest peak. Peaks at bases 128, 137, 144, 146 and 154 also show increased peak height in the presence of dUTP. This latter group of peaks are clearly identified in the pattern with dUTP whereas in the dTTP pattern these peaks would probably be difficult to detect in a full four color DNA sequencing analysis.

The above results are summarized in the table below.

| Dye-Labeled T-Terminator | ddTTP-EO-5FAM-B-dTMR2 | | ddTTP-EO-5FAM-B-dTMR2 | |
| --- | --- | --- | --- | --- |
| dTTP or dUTP Nucleotide | dTTP | dUTP | dTTP | dUTP |
| Amount of Dye-Labeled T-Terminator (pmol) | 20 | 20 | 12 | 12 |
| Mean Peak Height | 631 | 1791 | 635 | 1694 |
| Standard deviation in Peak Height | 355 | 841 | 319 | 662 |
| Relative Error in Peak Height | 0.56 | 0.47 | 0.5 | 0.39 |
| Noisy Peaks (%) | 33 | 22 | 18 | 0 |

The lower relative error and the reduction in the percentage of noisy peaks obtained when replacing dTTP with dUTP in a dye-terminator primer extension reaction using either of the above dye-labeled T-terminators indicates a more even peak height distribution which results in improved basecalling in an automated DNA sequencing system.

We claim:

1. A chain-termination type nucleic acid sequencing method comprising the steps of:

providing a template nucleic acid;

annealing an oligonucleotide primer to a portion of the template nucleic acid thereby forming a primer-template hybrid;

adding a primer-extension reagent to the primer-template hybrid for extending the primer and forming a primer extension product, the primer extension reagent including an unlabeled 2'-deoxyuridine-5'-triphosphate nucleotide or analog thereof in the absence of interfering amounts of a 2'-deoxythymidine-5'-triphosphate nucleotide; and adding a terminator to the primer-template hybrid for causing specific termination of the primer extension product.

2. The method of claim 1 wherein the terminator has a label attached thereto.

3. The method of claim 2 wherein the label is a fluorescent dye.

4. A kit for performing a chain-termination type nucleic acid sequencing method comprising:

an oligonucleotide primer;

a primer-extension reagent for extending the primer and forming a primer extension product, the primer extension reagent including an unlabeled 2'-deoxyuridine-5'-triphosphate nucleotide or analog thereof in the absence of interfering amounts of a 2'-deoxythymidine-5'-triphosphate nucleoside; and a terminator for causing specific termination of the primer extension product.

5. The kit of claim 6 wherein the terminator has a label attached thereto.

6. The kit of claim 5 wherein the label is a fluorescent dye.

7. A chain-termination type nucleic acid sequencing method comprising the steps of:

providing a primer-extension reagent to a primer-template hybrid for extending a primer and forming a primer extension product, the primer extension reagent including an unlabeled 2'-deoxyuridine-5'-triphosphate nucleotide or analog thereof in the absence of interfering amounts of a 2'-deoxythymidine-5'-triphosphate nucleotide; and adding a terminator to the primer-template hybrid for causing specific termination of the primer extension product.

* * * * *